United States Patent [19]

Pape

[11] 4,328,803

[45] May 11, 1982

[54] OPHTHALMOLOGICAL PROCEDURES

[75] Inventor: Lawrence G. Pape, Scarsdale, N.Y.

[73] Assignee: Opthalmic Systems, Inc., Long Island City, N.Y.

[21] Appl. No.: 198,290

[22] Filed: Oct. 20, 1980

[51] Int. Cl.$^3$ ............ A61B 17/00; A61K 31/70
[52] U.S. Cl. ............................. 128/276; 424/180
[58] Field of Search ................................. 128/276

[56] References Cited

U.S. PATENT DOCUMENTS 4,141,973  2/1979  Balazs ........................ 424/180

OTHER PUBLICATIONS

Healon, Product Information, Pharmacia.
Pape, L. G., The Use of Sodium Hyaluronate, *Ophthalmology*, vol. 87, 1980.
Binkhorst, C. D., American Intra-Ocular Implant Society, Journal, vol. 6 (4), Oct. 1980, pp. 340–341.

*Primary Examiner*—Robert W. Michell
*Assistant Examiner*—Nancy A. B. Swisher

*Attorney, Agent, or Firm*—Joseph Patrick Burke

[57] ABSTRACT

This disclosure is directed to improved opthalmological surgical procedures on the human eyeball characterized by initially utilizing ultra-pure hyaluronic acid in the form of a solution containing the sodium salt thereof, in a sufficient concentration thereof to protect delicate eye tissue and cells, e.g., 0.5 to 1.0 wt. % and higher, and thereafter, significantly diluting the concentration thereof in the aqueous media (natural and/or synthetic) within the anterior segment of the eye viz, in situ, so as to arrive at a concentration of said sodium salt of hyaluronic acid of less than 0.5 wt. % and more usually from about 0.1 to about 0.3 wt. % prior to closure. Hence a significant dilution from the initial higher concentrations by a factor of at least about 2:1 and more usually from about 3:1 to about 10:1 is effected. Hence the concentration of said sodium hyaluronate in the natural and/or synthetic aqueous media left within the eyeball at the surgical site after closure of the procedure ranges from about 0.1 to about 0.3 wt. % in the anterior chamber.

21 Claims, 2 Drawing Figures

OPHTHALMOLOGICAL PROCEDURES

BACKGROUND OF THE INVENTION

In the healthy eye, the intra-ocular pressure is maintained between certain physiological limits and these are considered as being normal. In the usual situations, the eye has normal intra-ocular pressures ranging from about 10 to 21 millimeters of mercury. Unfortunately, however, intra-ocular pressure can be abnormally high, and when the eye is harder than normal, this condition is known as glaucoma. Glaucoma is an undesirable condition because the elevated intra-ocular pressure causes damage to the optic nerve located in the back of eyeball. This elevated intra-ocular pressure impairs the circulation to the optic nerve and causes a loss of viable nerve fibers in the optic nerve. Consequently, the function of the optic nerve can be diminished, resulting in a loss of visual function of the eye. The range of increase of intra-ocular pressure can vary from mildly elevated, e.g., about 25 millimeters of mercury and slightly higher, to severe elevation, e.g., within the range from about 60 to 80 millimeters of mercury. Different adverse side effects can occur depending upon how acutely the pressure rises, the magnitude of the pressure elevation, the duration of said elevation in pressure, the underlying condition of the optic nerve and its blood supply, and whether or not the patient is recovering from ocular surgery.

Since elevations in intra-ocular pressure are independent of systemic body blood pressure, intra-ocular pressure elevations are comparatively localized within the eyeball, although the patient may experience systemic symptoms from elevated intra-ocular pressure such as headache, nausea, and vomiting.

Anatomically, the intra-ocular fluid known as aqueous humor is elaborated from the ciliary processes located in the posterior chamber. These ciliary processes are located behind the iris, or the colored part of the eye. Such aqueous humor has a very definite circulatory flow pattern within the eye. This circulatory pathway starts out where the aqueous humor is formed behind the iris. The fluid thus elaborated flows into the anterior chamber through the pupillary aperature of the eye and/or through a surgically created opening in the iris called an iridectomy. The aqueous humor ultimately drains into the angles of the anterior chamber and out through a network of collector channels within the wall of the eye.

The pathway for flow of the aqueous humor will be understood further in reference to the drawings, wherein the circumferential pathways of flow for the aqueous humor are illustrated by directional arrows in the anterior portion thereof.

FIG. 1 of the drawings is a cross-sectional view of a human eyeball illustrating the equator, visual axis, optic axis and key anatomical structures.

FIG. 2 is an anatomical flow chart illustrating the flow of aqueous humor in a normal eyeball through the main conduits and organs of flow, shown partly in section and appearing greatly enlarged.

As will be noted from FIG. 1 of the drawing, which is a cross-sectional view of the eyeball, the eyeball (10) has located at the posterior (rear) portion thereof, an optic nerve (11). Vitreous humor (22) occupies the vitreous body (13) between the retina (12) and lens (23). Proceeding from the optic nerve and lining approximately 70% of the inner surface area of the eyeball is the retina (12). Located anterior to the vitreous body (13) and within the posterior chamber (20) are the ciliary processes (14). It is from the ciliary processes that the aqueous humor (15) is produced.

Located in front of the iris, viz., the colored part of the eye (16), is a structure called the trabecular meshwork (17). This structure is located in the angle recess of the anterior chamber (21). It is through this trabecular meshwork that the aqueous humor percolates as it gains access through Schlemm's canal (18) to drainage networks which are in and/or on the wall of the eye.

The eye maintains a natural steady state flow of aqueous humor. In the normal healthy eye, there exists a homeostasis (balance) between the production of aqueous humor and drainage thereof. Depending upon how much aqueous humor is formed within the eye and the resistance to outflow in the path of flow of the aqueous humor at the trabecular meshwork site, the state of intra-ocular pressure within the eye can vary. When the resistance to outflow from the trabecular meshwork is high, the intra-ocular pressure rises within the eye. Intra-ocular pressure above the upper limit of normal, namely above about 21 millimeters of mercury, results in a condition of elevated intra-ocular pressure. Elevated intra-ocular pressure can have a variety of effects depending upon how abruptly the pressure is elevated and the circulatory status of the optic nerve in the back of the eye.

When the intra-ocular pressure rises abruptly to a very high level, the patient may experience pain. Pain usually arises when the pressure elevates very abruptly. When the pressure rises gradually, then the pain is not a common clinical symptom because of the fact that the eye has a chance to adapt to the elevated pressure. The comparative adequacy of the circulation to the optic nerve is a factor in determining the extent of ocular damage resulting from such elevated pressure. Although the aqueous humor drains in the front part of the eye in the angles of the anterior chamber, the intra-ocular pressure is constant throughout the eyeball, viz., the same pressure that is generated in the front part of the eye is also transmitted to the back part of the eye, specifically, to the optic nerve. This is how intra-ocular pressure damages the eye when a condition of glaucoma occurs. The circulation to the optic nerve is impeded and some of the nerve fibers in the optic nerve die, thus leading to a loss of visual function.

As noted previously, in the normal healthy eye, a basic homeostasis exists between the production of aqueous fluid and the drainage thereof. It is this steady state that determines the intra-ocular pressure at any given time within the eyeball. Hence, the intra-ocular pressure is dependent upon the rate at which the aqueous fluid is produced as compared to the rate at which it can drain from the eye. If the rate of aqueous humor drainage is impeded and the rate of aqueous production continues, then there will be a build-up of pressure inside the eye. A fundamental consideration of intra-ocular pressure is that, all other factors being equal, anything which obstructs the drainage of the aqueous humor from within the eye, e.g., by blocking the usual drainage channels in the angle recesses of the anterior chamber, or by blocking the egress of aqueous humor from the posterior chamber through the pupillary aperture and/or surgical iridectomy will cause intra-ocular pressure within the eye to elevate in the presence of a given constant production of aqueous humor.

Elevated intra-ocular pressure can be remedied by one or both of two approaches. One approach involves changing the rate at which the aqueous humor drains from the eye. If the outflow of aqueous fluid from the eye is increased, the intra-ocular pressure will diminish. Another way of lowering the intra-ocular pressure is to reduce the rate at which aqueous humor is produced within the eye. A combination of both methods can also be employed.

From the clinician's (surgeon's) point of view, the behavior of the intra-ocular pressure after completion of intra-ocular surgery is a primary post-operative consideration. The term "intra-ocular surgery" as used here, means any surgical procedure which enters the interior of the eyeball. Typical intra-ocular surgical procedures include, but are not necessarily limited to, cataract extraction, either by the intra-capsular or extra-capsular route and either with or without intra-ocular lens (23) implantations; corneal transplant procedures, either by themselves, or combined with cataract extraction and/or combined further with intra-ocular lens implanation; secondary implanation of an intra-ocular lens; phacoemulsification, which is a specialized way of performing an extra-capsular cataract extraction, and various glaucoma filtering procedures performed in an effort to lower intra-ocular pressure for glaucoma patients. The glaucoma filtering procedures can be combined with cataract surgery as well.

Intra-ocular surgical procedures can be classified into "closed," viz., tight incision procedures, such as cataract extraction, intra-ocular lens implantation, and corneal transplant procedures; and as "open" drainage procedures, e.g., those procedures applicable to surgery for glaucoma filtration. In all types of closed eye or tight incision, intra-ocular surgical procedures, there exists a primary concern for the possibility of abnormally elevated intra-ocular pressure post-operatively. The surgeon's main concern is the avoidance of such abnormally elevated intra-ocular pressure or the management thereof if it occurs.

The higher the intra-ocular pressure is post-operatively, the more alarming and undesirable is the situation. The higher the intra-ocular pressure elevation post-operatively, the more the patient will complain of pain. Such post-operative pain is clearly a definitive sympton for elevated intra-ocular pressure, which rises acutely over a short period of time post-operatively. When the intra-ocular pressure elevates acutely after surgery, the eyeball becomes acutely hard. This puts a great stress on any surgical incision which has been performed during the course of surgery. It is possible to have the incision site rupture as a result of generation of abnormally high intra-ocular pressures post-operatively. However, because these incisions are tightly closed under the control of the operating microscope using micro-surgical techniques, the incisions usually hold firm but other adverse effects can occur by virtue of the fact that this elevated if this abrupt rise in intra-ocular pressure is not relieved. This is how the production of pain occurs, because of continual pressure build-up within the eye without venting of the pressure.

One adverse effect of such intra-ocular pressure build-up is to cause a relative strangulation of the circulation to the optic nerve. This can cause blindness. In elderly patients who have hardening of the arteries and in whom the circulation in the optic nerve is borderline, post-operative elevation of intra-ocular pressure abruptly experienced over a significant period of time can cause significant percentages of sight loss, including in the most aggravated cases, blindness.

Consequently, an improved method of performing such tight incision, intra-ocular surgery so as to avoid adverse damage to the optic nerve has long been desired. Inasmuch as blindness is probably the most serious complication of tight incision intra-ocular surgical procedures, the behavior of the intra-ocular pressure post-operatively in all forms of intra-ocular surgery is of paramount importance.

One of the key structures in the eye which can be damaged because of elevated intra-ocular pressure is the cornea (19), viz., the window (front part) of the eye. Under conditions of normal intra-ocular pressure, the corneal thickness stays within normal values for any given time after eye surgery. When the intra-ocular pressure is abnormally elevated, however, the cornea becomes thicker than normal and the two outer layers of the cornea, known as the epithelium and stroma (not shown), become edematous (swollen). This condition is known as corneal edema. In fact, elevated intra-ocular pressures, post-intra-ocular surgery, can be manifested by the production of corneal edema. This is an abnormal (pathological) condition of the cornea and involves a thickening due to the elevated intra-ocular pressure forcing fluid to the cornea thereby causing it to swell. Ideally when the intra-ocular pressure is reduced to within normal levels, the corneal edema reverses itself. However, production of elevated intra-ocular pressure within the eye, regardless of the duration of time for which it persists, is not desirable because it causes trauma (injury) to the cornea resulting in a loss of certain corneal endotheleal cells thereby damaging the reserve of the cornea. Corneal endotheleal cells do not regenerate in the human eyeball. Consequently, it is very undesirable to have elevated intra-ocular pressure within the eye, not only because of damage to the optic nerve and the pain involved to the patient, but also because of pathological changes which can be inflicted upon the cornea. Thus, it will be realized that avoidance of elevated intra-ocular pressure is a long standing goal in ophthalomological surgery.

PRIOR ART

A paper published by E. A. Balazs, et al., entitled, "Hyaluronic Acid and Replacement of Vitreous and Aqueous Humor" published in the journal, *Modern Problems in Ophthalmology*, Volume 10, pages 3 to 21 (Karger, K. Basel, Switzerland, 1972), discusses the early history of the use of hyaluronic acid in various forms. The subject article reports studies conducted mostly in monkeys, but involving studies in humans as well, using a form of hyaluronic acid known as "Healon-H." These human studies involved intra-vitreal implantation of the "Healon-H" in the posterior segment (22). The conclusion of these studies was that excellent tolerance of humans for "Healon-H" was firmly established and that when high polymer hyaluronic acid of human origin, which is free from inflammatory substances, is implanted as a vitreous replacement in the form of an extremely viscous jelly, it does not cause increase in intra-ocular pressure. Of the seventy-one human cases studied, this paper indicates that there was one case where intra-ocular pressure increased, but was controlled by "Diamox" treatment. "Diamox" is a material which is administered systematically to control intra-ocular pressure, but the use of "Diamox" of course has its own complications. This one case was viewed by the authors as statistically insignificant and was treated as an anamolous situation.

U.S. Pat. No. 4,141,973 to Endre A. Balazs is directed to essentially a one weight percent solution of sodium salt of hyaluronic acid dissolved in a physiological buffer. The patentee states that the one weight percent solution of sodium hyaluronate should be left within the eye at the surgical site for a period of twenty-four hours post-operatively.

An article entitled, "Use of Na-Hyaluronate During Intra-Ocular Lens Implantation in Rabbits," appearing in the journal entitled, *Ophthalmic Surgery*, Volume 8, Number 6, pages 58 to 61, by David Miller, M.D., et al., discusses the use of sodium hyaluronate for replacing the aqueous media during intra-ocular lens implantation in rabbits. The observation is made on page 58, right column, of this paper that there is no evidence of abnormal elevation of intra-occular pressure appearing in forty rabbit eyes over a month of observation. It is also observed that there was also no statistical difference noted in the intra-ocular pressure of the groups of animals being studied.

The product monograph for the pharmaceutical material called "HEALON", a physiologically buffered one weight percent solution of sodium hyaluronate, which bears on page 17 thereof, a date of issue of March 1980, discusses the use of "HEALON" ®. On page 10, left column, of said monograph, there is an observation that the use of "HEALON" did not increase intra-ocular pressure post-operatively in humans according to a study conducted by Drs. Miller and Stegmann. The Miller, et al., paper was published in editorial form in the January 1980 issue of the *American Intra-Ocular Inplant Society Journal*, Volume 6, No. 1, pages 13–15 and entitled "Use of Na-Hyaluronate In Anterior Segment Eye Surgery." In these studies the entire anterior chamber of the eyeball was filled with the one weight percent buffered solution of sodium hyaluronate and these studies involved leaving a one weight percent solution of sodium hyaluronate in physiological aqueous buffers at the surgical site at the end of the surgical procedures.

There is, however, in the last paragraph on the left column of page 10 of said monograph, a reference to a controlled clinical study done by the present inventor wherein the development of intra-ocular pressures were noted in the immediate post-operative period with the observation that such increases were controlled with appropriate therapy as required. It is also stated that it was found that intracameral dilution of "HEALON" with balanced salt solution at the end of the surgical procedure eliminated the post-operative pressure elevation. It is this discovery of the existence of the acute elevated intra-ocular pressure caused by the use of a 1.0 wt. % concentration of sodium hyaluronate ("HEALON") and the effecting of significant dilution thereof prior to closure of the incision at the surgical site which is the essential gist of this invention.

An article entitled, "The Use of Sodium Hyaluronate (HEALON ®) in Human Anterior Segment Surgery" by the present inventor and Endre A. Balazs, appearing in *OPHTHALMOLOGY*, Volume 87, No. 7, July 1980, is directed to cataract extraction, without lens implantation (a closed procedure); three cases of keratoplasty (a closed procedure) and glaucoma filtration (open procedure). At the right column of page 704 of said Pape, et al., article, it is observed that in the cataract studies, the authors did not experience intra-ocular pressure elevations attributed to "HEALON." It is further stated that pressure elevations may be encountered under certain circumstances.

It was shortly after conducting the clinical studies reported on in said Pape, et al., article that the present inventor discovered a direct relationship between leaving the 1.0 wt. % solution of sodium hyaluronate within the anterior chamber at the end of the surgical procedure at the site and development of elevated intra-ocular pressure post-operatively.

DETAILED DESCRIPTION OF THE INVENTION

Figure 1:
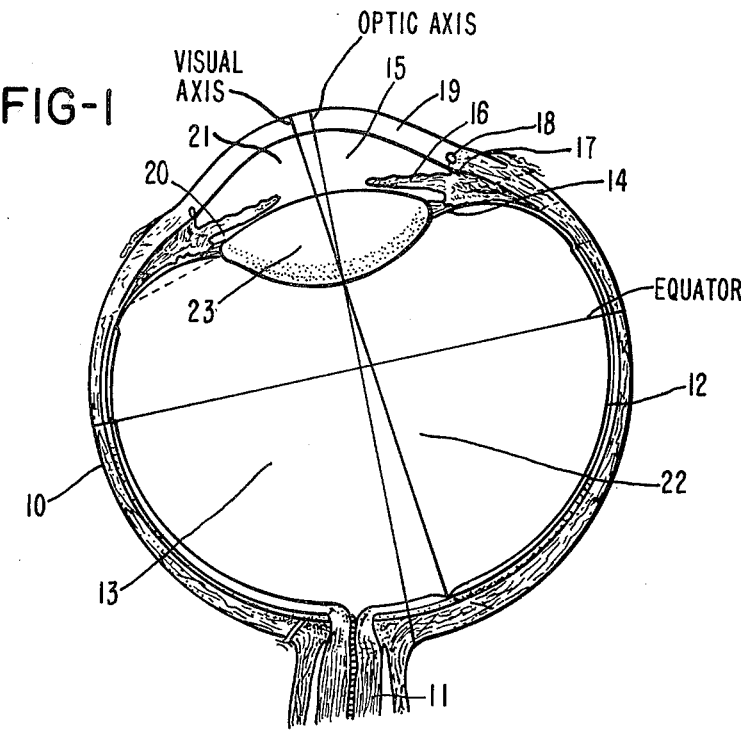
Figure 2:
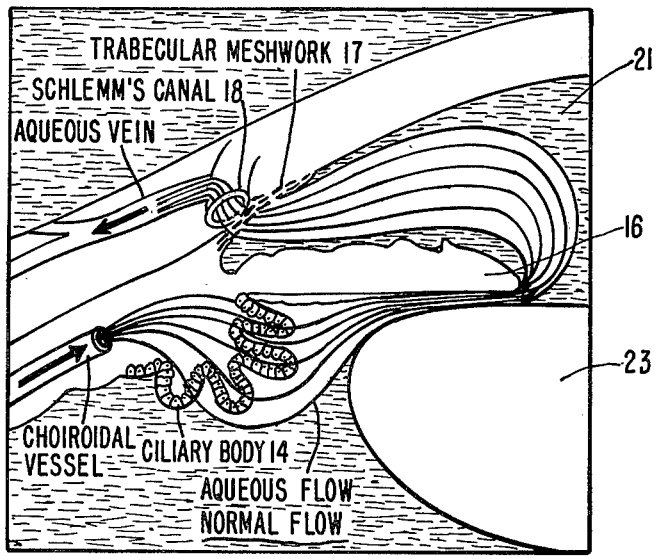

The present invention is based upon the discovery that when highly viscous solutions containing a sufficient concentration of sodium hyaluronate in physiologically buffered aqueous media to protect delicate eye tissue, e.g., 0.5 to 1.0 wt. % and higher, is introduced into the anterior chamber and left at the surgical site in such concentrations, the development of elevated intra-ocular pressure within the human eye occurs with very significant frequency. According to this invention, the development of such adverse elevated intra-ocular pressure can be avoided by a method involving initially using the sodium hyaluronate solution at 0.5 wt. % to 1.0 wt. % and higher concentration to obtain the protective benefits thereof during the surgery and then, prior to the close of the surgical site, effecting a dilution of concentration thereof, using either the available natural aqueous media present within the anterior chamber, viz., aqueous humor, or by diluting said concentration using buffered saline solution, or a combination of both media. In any event, the dilution is conducted such that there is effected a resulting dilution in site by a factor of at least 2:1 and more usually from about 3:1 to about 10:1 of said higher concentration "Healon" to leave within the anterior chamber at the end of the surgical procedure at the surgical site aqueous media containing "Healon" in an average concentration ranging from about 0.1 to about 0.3 wt. %.

There exists a wide spectrum of anterior segment ocular surgical procedures to which this invention is applicable. These procedures will include cataract extraction with intra-ocular lens implantation. This can be done either with an extra-capsular cataract extraction, intra-capsular cataract extraction or phacoemulsification and the type of intra-ocular lens that is used can vary depending upon the preference of the surgeon. Intra-ocular lens styles that can be used in this procedure include: iris-clipped and iris sutured intra-ocular lenses; anterior chamber angle fixated intra-ocular lenses and posterior chamber fixated intra-ocular lenses. This invention is also applicable to procedures of cataract extraction, alone. The type of cataract extraction employed can be either intra-capsular cataract extraction, extra-capsular cataract extraction or phacoemulsification. Another type of closed surgical procedure to which this invention is applicable are cases of penetrating keratoplasty. The type of penetrating keratoplasty procedure performed could be either phakic penetrating keratoplasty, aphakic penetrating keratoplasty, or pseudophakic penetrating keratoplasty. In addition, there is a wide range of anterior segment surgical procedures devoted to the repair of traumatic lacerations to the front part of the eye. Again, these fall under the classification of closed incision surgical procedures and the invention described herein is applicable to these procedures as well. The above described procedures are representative of closed incision types of surgical procedures to which this invention would have application, but they are not meant to be exclusive of other types of closed system surgical procedures.

The basic premise of this invention is the desirability of leaving at the surgical site at the close of the surgical procedure, a diluted concentration of sodium hyaluronate, namely, the diluted concentration of "HEALON" should be in the 0.1 to 0.3 wt. % range. This can be accomplished in what amounts to basically two ways and a combination thereof, depending upon the amount of sodium hyaluronate in the higher concentration that is initially introduced into the eye as part of the surgical procedure. Some surgical situations will call for the use of a very small aliquot of the higher concentration sodium hyaluronate, such as, e.g., from about 0.01 to about 0.05 cc. amounts. In this situation, since the volume of the anterior chamber is approximately 0.2 to 0.3 cc., this small aliquot of one percent solution would be diluted by the end of the surgical procedure by endogenous intracameral aqueous that is present within the eye, or that has found its way into the eye during the course of the surgical procedure.

However, in other surgical situations, it is necessary to introduce relatively a significantly larger volume of the higher concentration sodium hyaluronate solution into the eye. Such volumes would be in the 0.2 to 0.3 cc. range. In such situations it would be necessary to use exogenous synthetic aqueous, e.g., physiologically buffered saline solution, to effect a concentration dilution of this volume so that the end point that is the purpose of this invention is achieved, namely, that a concentration of about 0.1 wt. % to about 0.3 wt. % of sodium hyaluronate is left at the surgical site. The use of exogenous synthetic aqueous to dilute this relatively large volume of intra-cameral sodium hyaluronate solution can be achieved by a variety of surgical techniques.

It is possible to effect a dilution of the intra-cameral sodium hyaluronate solution by means of a carefully directed stream of irrigation saline solution, usually no more than about 3 to 4 cc. of synthetic aqueous saline solution is necessary to effect the appropriate dilution.

This saline solution can be flushed into the angles of the anterior chamber and into the center of the anterior chamber by means of delivery through a standard 19 to 30 gauge infusion cannula which is attached to an appropriate container for the synthetic aqueous. This is a standard surgical instrument available to an eye surgeon.

It is also possible to effect the desired dilution by means of other more mechanized devices which are presently available to the ophthalmic surgeon. These devices would include the use of the commercially available cavitron Irrigation and Aspiration Modality of the phacoemulsifier unit and any other type of irrigation and aspiration device, the purpose of which is to introduce a stream of synthetic aqueous solution in a controlled gentle manner into the anterior chamber and, subsequently, accomplish dilution of the contents of the anterior chamber so that a fluid exchange can occur whereby the highly vicous material is diluted and is replaced by an amount of synthetic aqueous salt solution so as to result in desired lowered concentration of sodium hyaluronate at the surgical site, viz., s 0.1 to 0.3 wt. % concentration or lower.

Care should be exercised when placing the original sodium hyaluronate solution, viz., that having a concentration of at least 1.0 wt. % of sodium hyaluronate so as to avoid inflow or access thereof to areas in the posterior chamber, behind the iris. Sequestration of this viscous material within the posterior chamber after closure of the surgical wound would lead to elevated intra-ocular pressure by interfering with the egress of aqueous fluids through the pupillary aperture and/or iridectomy opening.

The present invention has made mention of a desired concentration of sodium hyaluronate at the surgical site at the end of the procedure in the range of 0.1 to 0.3 wt. %. It is to be emphasized, however, that this represents simply to gross average type of concentration within the anterior chamber of the eye. It must be kept in mind that there may be localized areas of somewhat higher concentration of sodium hyaluronate with the net result being an average concentration of 0.1 wt. % to 0.3 wt. % range. It is also important to note that the presence of a localized area of relatively higher concentration of sodium hyaluronate in the 1% range, is not contrary to the scope of the present invention since the important factor is that the concentration thereof in critical regions such as the anterior chamber angle recesses and posterior chamber areas must be in a low range in the 0.1 to 0.3 wt. % range so as to allow the free and unobstructed flow of aqueous fluid from the posterior chamber into the anterior chamber and out through the trabecular meshwork. Localized areas of sodium hyaluronate concentration as high as 1.0% are in no way contrary to the scope of this invention, but reflect the viscoelastic nature of this material and the fact that the eye is a difficult model from which to draw a physical analogy since there really is no physical model which can be created to mimic the situations which obtain in the human eyeball at the time of ocular surgery. The salient points are that there must be a free and uninterrupted path for the flow of aqueous humor from the posterior chamber into the anterior chamber and out through the trabecular meshwork. It is important to avoid high average concentration of sodium hyaluronate in the posterior chamber as this would prevent fluid egress from the posterior chamber into the anterior chamber. In addition, there must not be a high concentration, i.e., 1% concentration of sodium hyaluronate in the anterior chamber angle recesses, that is, in regions that are adjacent to the filtration meshwork. These prerequisites insure an uninterrupted flow of aqueous humor, thereby maintaining normalcy of intra-ocular pressure postoperatively.

The invention will be illustrated in further detail in the examples which follow. In the examples, all parts, percents and ratios are by weight unless otherwise indicated.

EXAMPLE I (General Operative Procedure and Control Eyes)

A very important intra-ocular surgical procedure in which the present invention has much application is the operation of intra-ocular lens implantation following cataract extraction. The general overall surgical technique that can be used for intra-ocular lens implantation is as follows. Following induction of satisfactory general anesthesia, or if clinical situations so indicate, local anesthesia around the eyeball, the skin and lids about the eye are prepped with iodine and alcohol and draped as a sterile field. The conjunctival fornices are irrigated with standard antibiotic solutions and vasoconstrictor solutions. Following this, the eyelids are kept retracted to facilitate exposure of the surgical field. A superior rectus traction suture is usually passed under the belly of the superior rectus muscle. A conjunctival flap either of the fornix-based or limbal-based variety is next dissected. This flap can be of varying size depending upon the preference of the individual surgeon insofar as the ultimate size and location of the corneo-scleral incision. Following dissection of the conjunctival flap, the anterior chamber is entered by means of an abexterno incision using a surgical knife usually of the razor blade variety. Following entry into the anterior chamber of the eye, the surgical incision is then fashioned. The incision usually, but not always, extends over the superior 160 degrees of the limbus. Some surgeons may make a full 180 degree limbal incision, while others may make a very small limbal incision, particularly if the technique of phacoemulsification is to be used to remove the cataract. Nonetheless, the basic approach is to make an incision into the eye in the limbal zone so as to gain access to the cataract. Once the cataract incision has been made of the desired size and location, the attention is then directed to removing the cataract. Prior to actual cataract extraction, one or two openings in the iris, called iridectomies, are created surgically.

The cataract can be removed by whatever technique the surgeon desires, be that the intra-capsular technique, the planned linear extra-capsular technique or the phacoemulsification technique.

Following cataract extraction, attention is directed towards the implantation of the intra-ocular lens. In general, it is the object of intra-ocular lens implantation to introduce the artificial plastic implant lens into the desired position of fixation in the eye in such a manner so as to minimize trauma to adjacent ocular structures. In an effort to achieve this end, it is necessary to achieve control over the depth of the anterior chamber. This is done by passing and tying some corneo-scleral sutures so as to gain control of the incision and the depth of the anterior chamber. At the time that the lens is placed in the eye, care is taken so as to avoid snagging the lens on other structures in the eye. This is done with particular reference to avoiding rubbing the plastic lens against the overlying corneal endothelial layer, which is a layer of critically important and very delicate cells on the back of the cornea.

At the same time, attention must be directed to avoiding trauma to the underlying vitreous body, iris, and the posterior capsule should this have been left in place. The separation of these other ocular tissues is achieved through the use of corneo-scleral sutures and the injection and the injection of aqueous salt solution and/or an air bubble into the anterior chamber so as to create the surgical space necessary for intra-ocular lens implantation. It is usually by a combination of these three approaches that sufficient space can be created within the eye for implantation of the intra-ocular lens, whether an anterior chamber fixated lens, a posterior chamber fixated lens or an iris fixated lens. Following implantation of the intra-ocular lens using an air bubble and/or saline solution to maintain chamber depth, the corneo-scleral incision is then closed with multiple interrupted sutures or a running suture.

Following closure of the corneo-scleral incision, the conjunctival flap is also closed using interrupted or running sutures. The superior rectus traction suture is removed and antibiotic and corticosteriod medication is instilled into the eye and a protective dressing and shield put in place and the patient is then taken from the operating room.

This is the general technique that is presently employed today in the method of intra-ocular lens implantation following cataract extraction. The present invention demonstrates how this operative procedure can be facilitated by the use of lowered concentration of sodium hyaluronate at the surgical site on closure, namely the use of 0.1 to 0.3% solution of sodium hyaluronate at the surgical site in the anterior chamber at the close of surgery.

A composite group of eighteen control human eyes was studied in which no "Healon" was used at all. "Healon" is a commercially available physiologically buffered aqueous solution containing 1.0 wt. % sodium hyaluronate prepared as described in Balazs U.S. Pat. No. 4,141,973. An intra-ocular lens was implanted in each human following performance of two peripheral iridectomies and intra-capsular cataract extraction using the cryoprobe technique. The type of intra-ocular lens used was the Worst medallion-type lens with an iris suture of 10.0 Prolene for fixation. Eighteen such human eyes were used as a control group. With this technique, using only balanced salt solution and an air bubble to maintain tissue plane separation during the procedure, the following behavior of the intra-ocular pressure in the pre-operative and immediate post-operative state was noted. In the eighteen control human eyes, the average pre-operative intra-ocular pressure was 16.5 millimeters of mercury. On the first post-operative day, the average intra-ocular pressure that was measured in these eighteen control eyes was 17.4 millimeters of mercury (within the normal range).

EXAMPLE II (Sodium Hyaluronate Without Dilution at Closure)

This is a group of patients who had a procedure that was similar to that of Example I, namely, two peripheral iridectomies, intra-capsular cataract extraction with implantation of a Worst medallion type of iris-sutured lens using full anterior chamber filling with "HEALON" without dilution. In this group, a concentration of "HEALON" of 1.0 wt. % was left at the surgical site filling the exterior chamber.

Following extraction of the cataract by means of the intra-capsular technique with the cryo-probe, the anterior chamber was subsequently refilled to full aphakik depth by means of intra-cameral injection of "HEALON". The amount of the injection was approximately 0.2 to 0.3 cc. This intra-cameral injection of "HEALON" in one percent concentration resulted in a markedly deepened chamber and created an adequate surgical space in which intra-ocular lens implantation could be performed.

Once the anterior chamber had been completely reconstituted with "HEALON" an intra-ocular lens which was also coated with approximately 0.05 cc. of "HEALON" was put into position within the eye. The iris fixation suture of 10.0 Prolene was tightened, tied, and cut so as to allow the intra-ocular lens to be properly positioned within the eye. Following placement of the intra-ocular lens within the eye, the corneo-scleral incision was closed by means of interrupted sutures of 10-0 Nylon. Any "HEALON" that was lost during the placement of the intra-ocular lens was replaced. The "HEALON" was replaced in such a way so as to allow a reconstituted anterior chamber of full depth which was completely filled with a "HEALON" jelly of 1.0 wt. % concentration at the surgical site at the conclusion of the procedure in accordance with the method of said Balazs U.S. Pat. No. 4,141,973.

The method of intra-ocular lens implantation used in this patient group was identical to that used in Example I, with the exception that instead of using balance salt solution to reconstitute the anterior chamber volume, the entire anterior chamber volume was reconstituted using "HEALON" jelly in 1.0 wt. % sodium hyaluronate concentration.

Following this, the corneo-scleral incision was closed with twelve interrupted sutures of 10-0 Nylon material in exactly the same way as Example I. The conjunctive flap was closed by means of two interrupted 6-0 plain gut sutures as in Example I. Ten human eyes were operated on in this manner. In these human eyes that were treated with "HEALON" in 1.0 wt. % concentration and in which "HEALON" in 1.0 wt. % concentration was left in the anterior chamber at the surgical site at the close of the procedure, the following behavior of the intra-ocular pressure was observed. In these ten eyes, the average pre-operative pressures was 15.5 millimeters of mercury. On the first post-operative day, the average intra-ocular pressure in these ten eyes was 38.3 millimeters of mercury. It is of importance that eyes which had "HEALON" in a 1 wt. % concentration left at the surgical site showed extremely significant elevations in intra-ocular pressure. Two eyes in the group of ten that were operated on by this technique showed intra-ocular pressures on the first post-operative day between 61 and 70 millimeters of mercury. One eye showed intra-ocular pressure in the range of 50 to 60 millimeters of mercury. One eye showed intra-ocular pressure elevation in the 40 to 49 millimeter of mercury range. One eye showed intra-ocular pressure elevation in the 31 to 39 millimeter range. Four of these treated eyes showed intra-ocular pressure elevation in the 22 to 30 millimeter of mercury range. One of these eyes in the group in which the 1.0 wt. % "HEALON" solution was left at the surgical site showed intra-ocular pressure on the first post-operative day in the 10 to 21 millimeter of mercury range.

In summary, in patients in whose eyes 1.0 wt. % solution of sodium hyaluronate was left in the anterior chamber at the surgical site, in accordance with said Balazs patent, very marked elevations of intra-ocular pressure were noted on the first post-operative day.

EXAMPLE III

This example is a study of seven patients who underwent intra-capsular cataract extraction with implantation of an iris-sutured Worst medallion lens with the same technique employed in Example II. The only departure from the method described in Example II was that the 1.0 wt. % "HEALON" was diluted at the surgical site at the close of the surgical procedure. This was accomplished by irrigating the anterior chamber with approximately 3 to 4 cc (average) of commercially avialable balanced aqueous saline solution which was contained in a syringe or squeeze bottle to which an irrigation cannula had been attached. This allowed irrigation to be done in the recesses of the anterior chamber angle as well as in the center of the anterior chamber. Using this technique, irrigating the anterior chamber with approximately 3 to 4 cc of balanced salt solution was accomplished once one or two cardinal corneo-scleral sutures had been passed, tightened, tied and cut so as to secure prior control over the incision and the depth of the anterior chamber. It was thereby possible to effect a dilution of the 1.0 wt. % concentration of sodium hyaluronate at the surgical site. Using this technique, the "HEALON" concentration was reduced in the anterior chamber at the close of the procedure to approximately the 0.1 to 0.3 wt. % range. Following this dilution procedure, the corneo-sclereal section was closed in the exact same way as in Example II, by means of a total of twelve interrupted sutures of 10-0 Nylon material. Following this, the conjunctival flap was also closed, using two interrupted sutures of 6-0 plain gut. Antibiotic and cortiscosteroid ointment was placed in the eye and a sterile patch put in place. The patient was taken from the operating room.

Using this technique, the following behavior of intra-ocular pressure was observed. Seven human eyes comprised the group that underwent intra-capsular cataract extraction with implantation of a Worst medallion lens using the technique of dilution of the "HEALON" at the surgical site as described in this invention. In these seven patients, the average pre-operative intra-ocular pressure was 15.7 millimeters of mercury. On the first post-operative day, the average intra-ocular pressure of these seven patients measured 19.4 millimeters of mercury, well within the normal range.

VARIATIONS IN DILUTION

Endogenous dilution of the "Healon" ® that is used during intra-ocular lens implantation can be performed within the purview of this invention. Not all clinical situations call for total refilling of the anterior chamber with "Healon" prior to intra-ocular lens implantion. In a significant number of cases, the conditions at the time of surgery are such that there is no significant vitreous bulge, whether after intra-capsular or after extra-capsular cataract extraction.

In such cases of non-existent or only mild vitreous bulge, it can be desirable not to refill the anterior chamber with the higher concentration of "Healon" ®, e.g., 1.0 wt. %, but rather only to coat the intra-ocular lens surface therewith. In this way, only a small amount of said higher concentration "Healon" ® is introduced into the anterior chamber of the eye. In this situation, only a small amount of "Healon" ® coats the lens and the lens holder. Consequently, only a small amount of "Healon" ® can be introduced into the anterior chamber of the eye as the lens is put into position. The actual volume of 1.0 wt. %, "Healon" ® in this situation is relatively small and is approximately 0.05 cc. or less.

Once the intra-ocular lens is introduced into the eye with the protective coating of "Healon" ®, the rest of the volume of the anterior chamber is made up by endogenous aqueous. This is a combination of naturally produced aqueous humor by the ciliary processes which has occurred during the course of surgery as well as some artificial balance aqueous salt solution which has been introduced into the anterior chamber of the eye. In other words, the clinical circumstances can be such that it is not necessary to perform a total refilling of the anterior chamber during surgery and, consequently, only a small aliquot of concentrated, e.g. 1.0 wt. % sodium hyaluronate solution is introduced into the eye. The rest of the anterior chamber volume is comprised of said endogenous aqueous humor. This situation results in an already diluted "Healon" ® concentration at the surgical site in the range 0.1 to 0.3 wt. % and this dilution is accomplished by means of the endogenous saline. The achievement of this low concentration is a result of having used only a small amount of concentrated sodium hyaluronate jelly and diluting it to the concentration range of this invention by the means of endogeneously present aqueous humor prior to closure. Such use of such a small amount of "Healon" ® in intra-ocular lens implantation was found to result in no significant post-operative intra-ocular pressure elevation due to the dilution with endogenously present aqueous humor.

Essentially, similar avoidance of adverse elevated intra-ocular pressure has been achieved in accordance with this invention in a variety of surgical procedures using the method of this invention of dilution of the concentration of sodium hyaluronate solutions at the surgical site by means both of endogenous and exogenous dilution techniques such that the final concentration thereof at the surgical site at the close of surgery was in the range of about 0.1 to 0.3 wt. % concentration. These procedures have included penetrating keratoplasty procedures; cataract extractions using extracapsular, intra-capsular and phacoemulsification techniques; removal of intra-ocular lenses from the eye; and anterior segment reconstruction procedures following penetrating ocular trauma.

The overall aspect of this invention which governs all of these surgical procedures and others on the anterior segment of the eye (not specifically enumerated) is that all of the beneficial properties of the use of sodium hyaluronate can be achieved by initially using the sodium hyaluronate in a concentration sufficient to protect delicate eye tissues and cells during surgery, and then after this jelly has fulfilled its intended role of protecting delicate surfaces and intra-ocular structures, it is necessary to dilute the more concentrated solution either by endogenous or exogenous means such that at the end of the surgical procedure a concentration of sodium hyaluronate within about 0.1 to 0.3 wt. % is left at the surgical site.

A practical way that is useful in verifying the obtainment of 0.1 to 0.3 wt. % concentration of sodium hyaluronate at the operative site at the close of surgery is to observe the movement of cells in the aqueous humor in the anterior chamber on slit-lamp examination on the first post-operative day. This observation is usually made from 12 to 24 hours after closure of the surgical incision.

In non-"HEALON" operated eyes, in which balanced salt solution has been used to reconstitute the anterior chamber compartment at the end of surgery, immediate movement of aqueous humor cells, in normal convection patterns, is observed in the anterior chamber on slit-lamp examination on the first post-operative day.

In eyes in which a 1.0 wt. % solution of sodium hyaluronate has been left in the anterior chamber at the surgical site, on the first post-operative day, no such free movement of aqueous cells in accordance with convection currents is observed in the anterior chamber. As a result of the presence of viscous sodium hyaluronate at the surgical site, the aqueous cells are noted to be immobilized in the sodium hyaluronate viscous matrix that is present in the anterior chamber as a result of having left a 1.0 wt. % solution at the surgical site at the close of the procedure. No movement of aqueous cells are observed on either the first or second post-operative day as a rule.

However, when the sodium hyaluronate concentration has been reduced in accordance with this invention, either by endogenous or exogeneous dilution, on the first post-operative day normal convection currents and cell movements are observed in the aqueous humor of the anterior chamber. Aqueous cells are moving freely in the chamber in accordance with convection currents.

This observation of freely moving aqueous cells is made on the first post-operative day approximately 12 to 24 hours after the conclusion of the surgical procedure and as such can be used to indicate that the 1.0 wt. % "Healon" ® jelly has indeed been diluted to the 0.1 to 0.3 wt. % concentration range which avoids development of elevated intra-ocular pressure.

Although this invention has been described in terms of certain specific embodiments, it should be understood that modifications and variations may be made without departing from the spirit and scope of this invention as those skilled in the art will readily understand. Such modifications and variations are considered to be within the purview of the appended claims.

I claim:

1. In a method for protecting delicate human eye structures during ophthalmological surgical procedures by introducing into the anterior segment thereof a given volume of highly viscous physiologically buffered solution containing a sufficient concentration of sodium hyaluronate to protect delicate eye tissue, cells and structures, the improvement comprising diluting said volume in site thereby reducing the concentration thereof prior to closure such that abnormally high post-operative intra-ocular pressure within the human eye is avoided.

2. A method as in claim 1 wherein the gross concentration of said highly viscous sodium hyaluronate solution within the anterior segment at closure ranges from about 0.1 to about 0.3 wt. %.

3. A method as in claim 1 wherein the concentration of said highly viscous sodium hyaluronate solution as introduced into said anterior segment ranges from about 0.5 to about 1.0 wt. % and higher.

4. A method as in claim 1 wherein said dilution is effected endogenously.

5. A method as in claim 1 wherein said dilution is effected exogenously.

6. A method as in claim 5 wherein said exogenous dilution is conducted by directing a physiologically buffered aqueous saline solution in the region of said previously introduced highly viscous sodium hyaluronate solution.

7. A method according to claim 1 wherein said dilution is by a factor of at least 2:1.

8. A process according to claim 1 wherein said dilution is by a factor ranging from about 3:1 to 10:1.

9. A method as in claim 1 wherein said surgical procedure is performed within the anterior chamber of the eye.

10. A method as in claim 1 wherein said surgical procedure involves an intra-ocular implant of a lens within the eye.

11. A method according to claim 10 wherein said implantation is effected by iris fixation.

12. A method according to claim 10 wherein said lens implantation is conducted by anterior chamber angle fixation.

13. A method according to claim 10 wherein said lens implantation is conducted by posterior chamber fixation.

14. A method as in claim 1 wherein said surgical procedure involves a corneal transplant within the eye.

15. A method as in claim 1 wherein said surgical procedure involves a cataract extraction from the eye.

16. A method as in claim 15 wherein said cataract extraction involves an intra-capsular extraction.

17. A method according to claim 15 wherein cataract extraction is obtained by extra-capsular extraction.

18. A method according to claim 15 wherein said cataract extraction is effected by phacoemulsification.

19. A method according to claim 15 wherein said cataract is removed by intra-capsular cataract extraction.

20. A method according to claim 15 wherein said cataract is removed by extra-capsular cataract extraction.

21. A method according to claim 15 wherein said cataract is removed by phacoemulsification.

* * * * *

REEXAMINATION CERTIFICATE (2179th)

United States Patent [19]

Pape

[11] B1 4,328,803

[45] Certificate Issued  Jan. 11, 1994

[54] OPTHALMOLOGICAL PROCEDURES

[75] Inventor: Lawrence G. Pape, Scarsdale, N.Y.

[73] Assignee: Opthalmic Systems, Inc., Long Island City, N.Y.

Reexamination Request:
No. 90/002,673, Mar. 13, 1992

Reexamination Certificate for:
Patent No.: 4,328,803
Issued: May 11, 1982
Appl. No.: 198,290
Filed: Oct. 20, 1980

[51] Int. Cl.$^5$ .................. A61M 1/00; A01N 43/04
[52] U.S. Cl. ........................... 604/28; 604/49; 514/54; 514/912; 128/898
[58] Field of Search ..................... 604/49; 128/898

[56] References Cited

U.S. PATENT DOCUMENTS 3,589,363  2/1979  Banko .
4,141,973  2/1979  Balazs .

OTHER PUBLICATIONS

Fechener, P. U., "Preparation of 2% Hydroxypropyl Methylcellulose for Viscous Surgery," *Am. Intraocular Implant Soc. J.*, vol. II pp. 606–607 (1985).

Physicians' Desk Reference For Opthalmalogy, 1979/1980, pp. 96–97.

M. A. Galin, et al., "Cataract Extraction and Intraocular Pressure", *Trans. Ophthal. Soc. U.K.* 98: pp. 124–127 (1978).

Alpar, et al., "Viscoelastic and Other Materials for Cushioning the Anterior Chamber and Coating the Intraocular Lens" *Fechner's Intraocular Lenses,* (Fechner, ed.) Chapt. 11, pp. 118–129 (Thieme Inc., 1986).

Steele, A. D. McG., "Hydroxypropylmethylcellulose used as a Viscoelastic Fluid in Ocular Surgery," in *Viscoelastic Materials,* (Rosen, ed.) pp. 161–163 (Pergamon Press, 1986).

Hammer, M. E. and Burch, T. G., "Viscous Corneal Protection by Sodium Hyaluronate, Chondroitin Sulfate, and Methylcellulose" *Invest. Ophthal. & Vis. Sci.,* 25:(11) 1329–32 (Nov. 1984).

Aron-Rosa, D., et al. "Methylcellulose Instead of Healon ® in Extracapsular Surgery with Intraocular Lens Implantation" *Am. Acad. Ophthal.,* 90:(10) 1235–38 (Oct. 1983).

MacRae, S. M., et al., "The Effects of Sodium Hyaluronate, Chondroitin Sulfate, and Methylcellulose on the Corneal Endothelium and Intraocular Pressure," *Am. J. Ophthalm.,* 95: 332–41 (1983).

Fechner, "The Use of Methylcellulose During Lens Implantation," *Am. Intraocular Implant Soc. J.* 6: 368–69 (Oct. 1980).

Kazdan, et al., "A Technique for Experimental Angle Block in Rabbits Avoiding the Paracentesis Reflex," *Am. J. Ophth.,* 59: 463–65 (1965).

Fleming, et al., "Studies of the Irritating Action of Methylcellulose," *Arch. Ophthal.,* 61: 565–67 (1959).

Lorenzetti, et al., "Procedure for Evaluating Drug Effects on Increased Intraocular Pressure," *Arch Ophthal,* vol. 78, pp. 624–628 (1967).

Barany, E. H., "The Action of Different Kinds of Hyaluronidase on the Resistance to Flow Through the Angle of the Anterior Chamber", *Acta Ophthalmologica,* vol. 34, pp. 397–403 (1956).

*New and Controversial Aspects of Retinal Detachment,* 1968, Alice McPherson (Editor) pp. 380–381, 388–389, 490–493.

Balazs, et al., "Hyaluronic Acid and Replacement of Vitreous and Aqueous Humor," *Modern Problems of Ophthalmology,* vol. 10, 3–21 (1972).

Francois, J., "The Importance of Mucopolysaccharides in Intraocular Pressure Regulation," *Investigative Ophthalmology,* vol. 14, No. 3, pp. 173–176 (Mar., 1975).

Fechner P. V., "Methylcellulose in Lens Implantation," *American Intraocular Implant Soc. J.,* vol. 3, pp. 180–181 (1977).

Comper and Laurent, "Physiological Function of Connective Tissue Polysaccharides," *Physiological Reviews,* 58:255–315, 300–01 (Jan. 1978).

Drews, "The Management of Patients with Intraocular Lenses — Guidelines for those who do not perform this operation," *Ophthalmic Surgery,* 10(2):56–64 (1979).

HEALON, Product Information, Pharmacia.

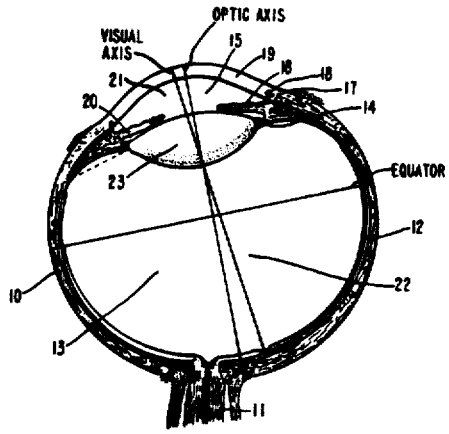

Pape, L. G. and Balazs, E. A., "The Use of Sodium Hyaluronate (Healon ®) in Human Anterior Segment Surgery", *American Academy of Ophthalmology*, vol. 87, pp. 699-705 (1980).

Binkhorst, C. D., "Inflammation and Intraocular Pressure after the use of Healon ® in Intraocular Lens Surgery," *Am Intra-Ocular Implant Soc J*, vol. 6(4), pp. 340-341 (Oct. 1980).

*Primary Examiner*—C. Fred Rosenbaum

[57]     ABSTRACT

This disclosure is directed to improved opthalmological surgical procedures on the human eyeball characterized by initially utilizing ultra-pure hyaluronic acid in the form of a solution containing the sodium salt thereof, in a sufficient concentration thereof to protect delicate eye tissue and cells, e.g., 0.5 to 1.0 wt. % and higher, and thereafter, significantly diluting the concentration thereof in the aqueous media (natural and/or synthetic) within the anterior segment of the eye viz, in situ, so as to arrive at a concentration of said sodium salt of hyaluronic acid of less than 0.5 wt. % and more usually from about 0.1 to about 0.3 wt. % prior to closure. Hence a significant dilution from the initial higher concentrations by a factor of at least about 2:1 and more usually from about 3:1 to about 10:1 is effected. Hence the concentration of said sodium hyaluronate in the natural and/or synthetic aqueous media left within the eyeball at the surgical site after closure of the procedure ranges from about 0.1 to about 0.3 wt. % in the anterior chamber.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 4 having been finally determined to be unpatentable, are cancelled.

Claims 2, 3, 5, 7, 8, 9, 10 and 14–15 are determined to be patentable as amended.

Claims 6, 11, 12, 13 and 16–21, dependent on an amended claim, are determined to be patentable.

2. A method as in claim [1] *5* wherein the gross concentration of said highly viscous sodium hyaluronate solution within the anterior segment at closure ranges from about 0.1 to about 0.3 wt. %.

3. A method as in claim [1] *5* wherein the concentration of said highly viscous sodium hyaluronate solution as introduced into said anterior segment ranges from about 0.5 to about 1.0 wt. % and higher.

5. [A method as in claim 1] *In a method for protecting delicate human eye structures during ophthalmological surgical procedures by introducing into the anterior segment thereof a given volume of highly viscous physiologically buffered solution containing a sufficient concentration of sodium hyaluronate to protect delicate eye tissue, cells and structures, the improvement comprising diluting said volume in site thereby reducing the concentration thereof at the end of the surgical procedure prior to closure such that abnormally high post-operative intra-ocular pressure within the human eye is avoided* wherein said dilution is effected exogenously.

7. A method according to claim [1] *5* wherein said dilution is by a factor of at least 2:1.

8. A process according to claim [1] *5* wherein said dilution is by a factor ranging from about 3:1 to 10:1.

9. A method as in claim [1] *5* wherein said surgical procedure is performed within the anterior chamber of the eye.

10. A method as in claim [1] *5* wherein said surgical procedure involves an intra-ocular implant of a lens within the eye.

14. A method as in claim [1] *5* wherein said surgical procedure involves a corneal transplant within the eye.

15. A method as in claim [1] *5* wherein said surgical procedure involves a cataract extraction from the eye.

* * * * *